(12) United States Patent
Bergmann

(10) Patent No.: US 7,569,209 B2
(45) Date of Patent: Aug. 4, 2009

(54) METHOD FOR DIAGNOSIS OF SEPSIS BY DETERMINATION OF S100B

(75) Inventor: Andreas Bergmann, Berlin (DE)

(73) Assignee: B.R.A.H.M.S. Aktiengesellschaft, Hennigsdorf (DE)

( * ) Notice: Subject to any disclaimer, the term of this patent is extended or adjusted under 35 U.S.C. 154(b) by 854 days.

(21) Appl. No.: 10/496,155

(22) PCT Filed: Nov. 27, 2002

(86) PCT No.: PCT/EP02/13393

§ 371 (c)(1),
(2), (4) Date: Nov. 5, 2004

(87) PCT Pub. No.: WO03/048778

PCT Pub. Date: Jun. 12, 2003

(65) Prior Publication Data

US 2005/0064506 A1 Mar. 24, 2005

(30) Foreign Application Priority Data

Dec. 4, 2001 (EP) .................................. 01128849

(51) Int. Cl.
*A61K 49/00* (2006.01)
*A01N 63/00* (2006.01)
*A61K 39/38* (2006.01)
*G01N 33/554* (2006.01)
*G01N 33/53* (2006.01)

(52) U.S. Cl. .................... 424/9.1; 424/93.4; 424/184.1; 435/7.32; 435/7.31

(58) Field of Classification Search ........................ None
See application file for complete search history.

(56) References Cited

U.S. PATENT DOCUMENTS

| 5,639,617 A | 6/1997 | Bohuon ...................... 435/7.1 |
| 5,660,994 A | 8/1997 | Bruder-Heid et al. ...... 435/7.23 |

FOREIGN PATENT DOCUMENTS

| DE | 198 47 690 A1 | 4/2000 |
| DE | 101 19 804 A1 | 10/2002 |
| DE | 101 30 985 A1 | 1/2003 |
| DE | 101 31 922 A1 | 1/2003 |
| EP | 1 318 403 B1 | 7/2004 |
| WO | WO 00/22439 | 4/2000 |
| WO | WO 02/085937 A2 | 10/2002 |
| WO | WO 03/002600 A1 | 1/2003 |
| WO | WO 03/005035 A1 | 1/2003 |

OTHER PUBLICATIONS

Hauschild et al. (British Journal of Dermatology, 1999, vol. 140 No. 6, pp. 1065-1071).*
Bosserhoff et al. (Cancer Research, 1997, vol. 57, pp. 3149-3153).*
Aird, "The Hematologic System as a Marker of Organ Dysfunction in Sepsis," *Mayo Clin, Proc.*, 78:869-881, 2003.
Assicot, et al., "High Serum Procalcitonin Concentrations in Patients with Sepsis and Infection," *Lancet*, 341(8844):515-518, 1993.
Beishuizen et al., "Endogenous Mediators in Sepsis and Septic Shock," *Advances Clin. Chem.*, 33:55-131, 1999.
Bertsch et al., "Protein S-100B: A Serum Marker for Ischemic and Infectious Injury of Cerebral Tissue," *Clin. Chem. Lab Med.*, 39(4):319-323, 2001.
Carrigan et al., "Toward Resolving the Challenges of Sepsis Diagnosis," *Clin. Chem.*, 50(8):1301-1314, 2004.
Donato, "Functional Roles of S100 Proteins, calcium-Binding Proteins of the EF-Hand Type," *Biochim. Biophys. Acta*, 1450:191-231, 1999.
Gabay and Kushner, "Acute-Phase Proteins and Other Systemic Responses to Inflammation," *New Engl. J. Med.*, 340(6):448-454, 1999.
Hotchkiss and Karl, "The Pathophysiology and Treatment of Sepsis," *N. Engl. J. Med.*, 348(2):138-150, 2003.
Jäckel, "S-100β-Protein im Serum als Tumormarker beim malignen Melanom," *Hautarzt*, 50:250-256, 1999.
Karzai, et al., "Procalcitonin—A New Indicator of the Systemic Response to Severe Infections," *Infection*, 25:3-8, 1997.
Kerkhoff et al., "Novel Insights Into Structure and Function of MRP8 (S100A8) and MRP14 (S100A9)," *Biochim. Biophys. Acta*, 1448:200-211, 1998.
Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).

(Continued)

*Primary Examiner*—Robert A Zeman
(74) *Attorney, Agent, or Firm*—Heslin Rothenberg Farley & Mesiti P.C.

(57) ABSTRACT

Method for early differential diagnosis and detection, for prognosis and for assessing the severity and for therapy-accompanying assessment of the course of sepsis and sepsis-like systemic infections, in which, preferably with determination of at least one further parameter suitable for sepsis diagnosis, the amount of S100B in a biological fluid of a patient in whom a sepsis is present or sepsis is suspected is determined and conclusions with regard to the presence, the expected course, the severity and/or the success of initiated measures for the therapy of sepsis are drawn from the determined amount of S100B.

4 Claims, 2 Drawing Sheets

OTHER PUBLICATIONS

Figure 1:
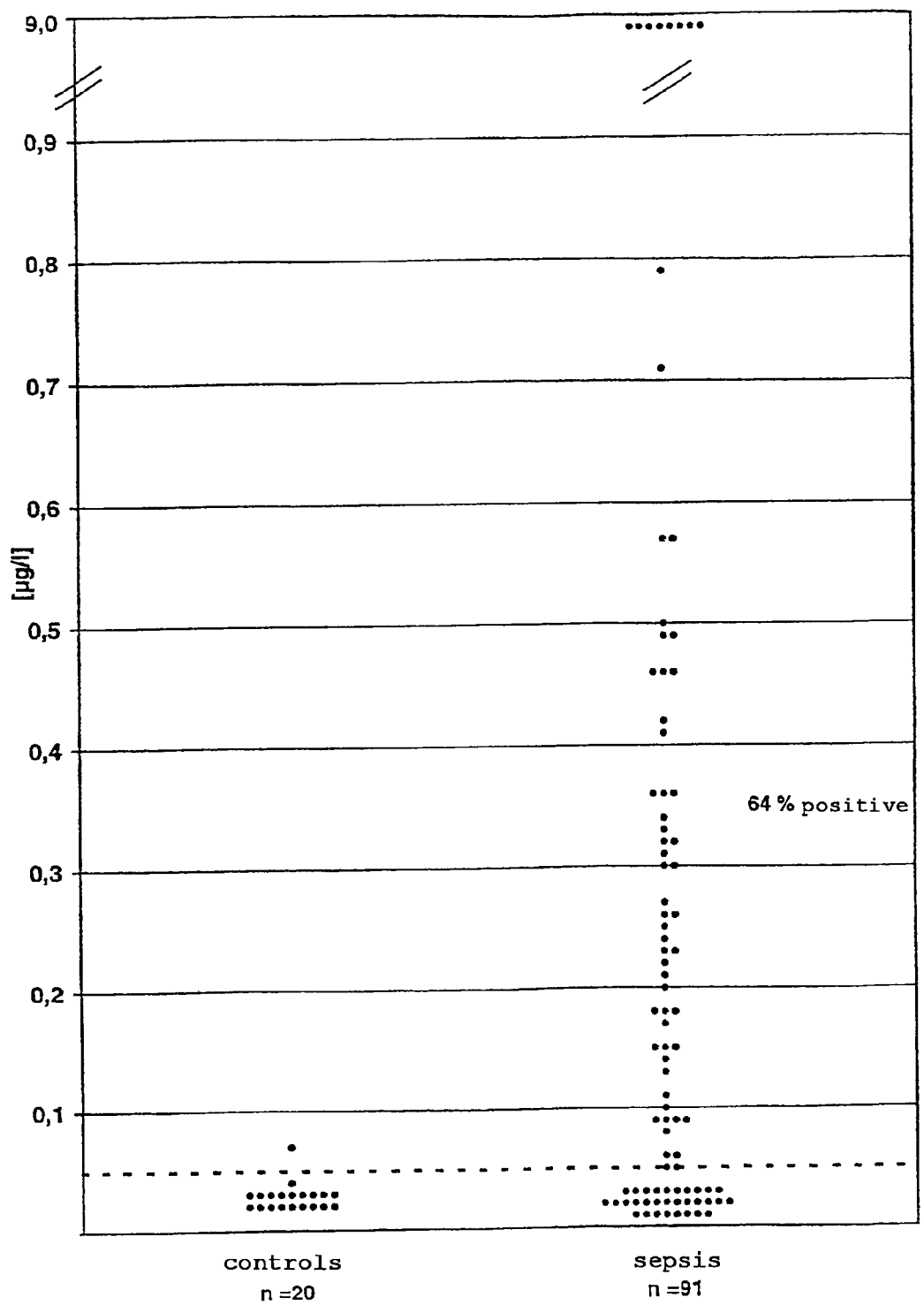

Nagamatsu et al., "Cerebrospinal Fluid Levels of S-100b Protein and Neuron-Specific Enolase in Chronic Inflammatory Demyelinating Polyneuropathy," *Acta Neurol. Scand.*, 91:483-487, 1995.

Oberholzer et al., "Sepsis Syndromes: Understanding the Role of Innate and Acquired Immunity," *Shock*, 16(2):83-96, 2001 (Abstract only).

Oczenski et al., "Procalcitonin: A New Parameter for the Diagnosis of Bacterial Infection in the Peri-Operative Period," *Eur. J. Anaesthesiol.*, 15:202-209, 1998.

Passey et al., "S100A8: Emerging Functions and Regulation," *J. Leukoc. Biol.*, 66:549-556, 1999.

Redl et al., "Procalcitonin Release Patterns in a Baboon Model of Trauma and Sepsis: Relationship to Cytokines and Neopterin," *Crit. Care Med.*, 28(11):3659-3663, 2000.

Redl and Schlag, "Non-Human Primate Models of Sepsis," *Sepsis*, 2:243-253, 1998.

Reinhart et al., "Sepsis Und Spetischer Schcok," *Intensivmedizin*, 756-760, 2001.

International Search Report for EPO Application No. 01128849.5, mailed Jun. 4, 2002.

International Search Report for PCT Application No. PCT/EP 02/13393, mailed Nov. 27, 2002.

* cited by examiner

METHOD FOR DIAGNOSIS OF SEPSIS BY DETERMINATION OF S100B

The present application is a nationalization of PCT Application Ser. No. PCT/EP02/133393, filed Nov. 27, 2002, which claims priority to European application No. 01128849.5, filed Dec. 4, 2001.

The invention relates to a novel method for sepsis diagnosis, in which or in the course of which the calcium-binding protein S100B is determined in a human serum.

The invention is based on the detection for the first time of greatly increased concentrations of S100B in sera of human patients in whom a bacterial sepsis had been diagnosed on the basis of clinical findings and simultaneously increased serum concentrations of the known sepsis marker procalcitonin.

The present invention has its origin in intensive research work by the Applicant in relation to further improvements of the diagnosis and therapy of inflammations of infectious aetiology and sepsis.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of numerous serious chronic and acute diseases of individual tissues, organs, organ parts and tissue parts.

In sepsis or septic shock, inflammation-specific reaction cascades spread in an uncontrolled manner over the whole body and may become life-threatening in the context of an excessive immune response. Regarding the current knowledge about the occurrence and the possible role of individual groups of endogenous sepsis-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, New York, 2001, 756-760, where a modern definition of sepsis is given. In the context of the present Application, the term sepsis used is based on the definitions given in the stated references.

Whereas at least in Europe the systemic bacterial infection detectable by a positive blood culture long characterized the term sepsis, sepsis is now primarily understood as being systemic inflammation which is caused by infection. Said transformation of the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known or presumed to be involved in an inflammatory process, ones which are suitable for purposes of clinical sepsis diagnosis are in particular those which occur with high sensitivity and specificity in sepsis or certain phases of a sepsis, or whose concentrations change in a dramatic and diagnostically significant manner and which moreover have the stabilities required for routine determinations and reach high concentration values. For diagnostic purposes, the reliable correlation of the pathological process with the respective biomarker is of primary importance, without there being any need exactly to know its role in the complex cascade of the endogenous substances involved in the inflammatory process.

A known, endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis and for early distinguishing of a sepsis caused by infection from severe inflammations which have other causes. The determination of procalcitonin is furthermore particularly valuable for the therapy-accompanying observation of the course of a sepsis. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP 0 656 121 B1 and U.S. Pat. No. 5,639,617. Reference is hereby made to said patents and to early references mentioned in said publications for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329-334; and M. Oczenski et al., "Procalcitonin: a new parameter for the diagnosis of bacterial infection in the peri-operative period", European Journal of Anaesthesiology 1998, 15, 202-209; and furthermore H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", in: Sepsis 1998; 2:243-253; and the further literature references cited therein, as typical of recent published reviews.

The availability of the sepsis marker procalcitonin has given considerable impetus to sepsis research, and intensive efforts are now being made on the part of the Applicant to find further biomarkers which can supplement the procalcitonin determination and/or are capable of providing additional information for purposes of fine diagnosis or differential diagnosis of septic diseases. Attempts are therefore being made in particular to find further biomarkers for sepsis diagnosis, the levels of which in serum or plasma are regularly increased but which, in their determination, do not simply duplicate the results of the procalcitonin determination but provide additional information, in particular about the stage of the sepsis process, i.e. information preferably to be associated with the course of the sepsis as a function of time, and/or about the initial organ or main organ of a septic process, i.e. localizing information. The aim is finally the selection of a set of sepsis parameters which are simultaneously determined in sepsis patients or potential sepsis patients, for example with the use of the so-called chip technology or immunochromatographic methods ("point of care" or POC determinations), and in their totality provide an information pattern which clearly surpasses the information value of the determination of only a single parameter.

The search for potential novel sepsis biomarkers is, however, complicated by the fact that frequently very little or nothing is known about the exact function or about the exact reasons for the occurrence of certain endogenous substances which are involved in the inflammation or sepsis process.

Since the endogenous substances present in higher concentration during sepsis are part of the complex reaction cascade of the body, not only are such substances also of diagnostic interest but attempts are also currently being made, with considerable effort, to intervene therapeutically in the sepsis process by influencing the formation and/or the concentration of individual substances of this type, in order, for example, to stop as early as possible the systemic spread of the inflammation, which spread is observed during sepsis. In this context, endogenous substances which have been shown to have been involved in the sepsis process are also to be regarded as potential therapeutic targets.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin significantly increased but also significantly increased concentrations can be observed for other substances which may be included among the peptide prohormones. The peptide prohormones pro-enkephalin, pro-gastrin-releasing peptide (proGRP), pro-endothelin-1, pro-brain-natriuretic peptide (pro-BNP), pro-atrial natriuretic peptide (pro-ANP), pro-leptin, pro-neuropeptide-Y, pro-somatostatin, pro-neuropeptide-YY, pro-interleukin-6 or pro-interleukin-10 may be mentioned in this context. While the phenomenon described is well documented, the causes of the increase in the concentrations of prohormones in sepsis are still substantially unexplained.

In the present Application, a result of another hypothetical approach to the search for further biomolecules suitable for sepsis diagnosis is now reported. It is based on the results of measurements of the physiological concentrations of biomarkers, which have been regarded to date as tumour markers and therefore determined clinically substantially for purposes of tumour diagnosis, in biological samples, in particular serum samples, of sepsis patients in whom no clinical findings at all indicated the presence of tumours.

Surprisingly, it was found that, in the case of a bacterial sepsis, some biomolecules regarded to date as typical tumour markers are also significantly increased. This indicates that these are not formed in a tumour-specific manner but are a sign of a systemic critical physiological process which also affects tissues or organs which release these tumour markers. Although, as shown in this Application and simultaneously filed further Applications, the concentrations of the biomolecules in question are increased in the case of sepsis with high sensitivity, there is at the same time no quantitative correlation of the measured value with the likewise significantly increased procalcitonin concentrations, i.e. in individual patients both parameters are found to have increased but in some cases to very different extents.

The present invention is based on the evidence, obtained for the first time, that significantly increased physiological concentrations of the protein S100B are found in human sera in the case of bacterial sepsis, making this parameter, in particular in combination with the determination of further sepsis parameters, suitable for the differential diagnosis of sepsis.

It was not known to date that the concentrations of S100B in biological fluids, in particular the serum concentrations, are significantly increased in the case of a bacterial sepsis and that a determination of the concentration of S100B could therefore also be important for the diagnosis of sepsis.

On the basis of the present invention, it is possible to use the determination of S100B also in a diagnostic sepsis detection method. Of particular interest is the suitability of S100B as a prognosis marker and marker for the monitoring of the course of sepsis, in particular in a combination measurement with other markers.

In addition to a combination with a procalcitonin measurement, a combination of the measurement of S100B with the determination of other markers for sepsis and systemic inflammations, which have been regarded to date as typical tumour markers, is particularly suitable especially with CA 19-9, CA 125 or proteins of the S100A group, or with the determination of the novel sepsis markers inflammin (DE 101 19 804.3) and CHP (DE 101 31 922.3) described in the prior unpublished German Patent Applications of the Applicant which are mentioned below, and/or with the determination of soluble cytokeratin fragments, in particular the recently found soluble cytokeratin-1 fragments (sCY1F; DE 101 30 985.6) and the parameters CYFRA-21 or TPS known as tumour markers and/or one or more of the above-mentioned prohormones. A simultaneous determination of the known inflammation parameter C-reactive protein (CRP) may also be provided. On the basis of the novel results described in these and in the parallel Applications, a combination with measurements of known biomolecules or biomolecules still to be found is also to be considered generally for the fine diagnosis of sepsis, said biomolecules being suitable as sepsis markers and/or tissue- or organ-specific inflammation markers.

The content of said prior Applications of the Applicant is to be regarded as part of the disclosure of the present Application by the express reference to these Applications.

S100B is defined as a protein from the group consisting of the so-called "S100" proteins which, as their name implies, have the property of remaining in solution even at 100% saturation with ammonium sulphate at neutral pH (solubility 100%). They belong to the calcium-binding proteins, which are usually localized in cytoplasma. However, some S100 proteins, including S100B, also occur in the extracellular space. Regarding the S100 proteins and their known properties, functions and positive and negative effects in various pathological processes, in particular those of the brain and central nervous system, reference may be made to various review articles, of which, for example, the review articles by Rosario Donato in The International Journal of Biochemistry & Cell Biology 33 (2001) 637-668 and in Biochim. Biophys. Acta 1450 (1999) 199-231, which summarize extensive relevant scientific literature, are mentioned herein. Some S100 proteins, in particular the proteins S100A8 and S100A9, when they occur in the extracellular space, also appear to play a regulatory, in particular activating or inhibitory, role in inflammatory reactions (cf. for example R. J. Passey, J. Leukoc. Biol. 66 (1999), 549-556, or C. Kerkhoff et al., Biochim. Biophys. Acta 1448 (1998) 200-211).

A determination of S100B in the so-called liquor and in the serum is recommended for diagnostic purposes in patients with brain lesions and affects the extent of the damage caused, for example, by an ischaemia. Since brain damage also occurs as a consequence of systemic infection with the fungus *Candida albicans*, an experimentally induced *Candida albicans* infection of mice serves for investigating the relationship between brain damage caused by fungal infection and S100B release into the serum of the mice (cf. Thomas Bertsch et al., Clin. Chem. Lab. Med 2001, 39(4):319-323). However, S100B is also a special tumour marker, and in particular S100B is measured as a tumour marker in the case of malignant melanoma, especially for prognostic purposes (cf. for example Andreas Jäckel et al., Hautarzt, 1999, 50:250-256). Because of its use as a tumour marker, S100B was determined in the course of the experiments described in more detail below, in the sera of patients in whom a bacterial sepsis had been diagnosed.

To our knowledge, no systemic S100B measurements have as yet been carried out in human patients suffering from a bacterial sepsis, and nothing has yet been disclosed regarding significantly increased measured values of the tumour marker S100B in patients suffering from bacterial sepsis or systemic inflammations caused by infection.

A substantial increase in the S100B concentrations in the predominant number of sepsis patients was found for the first time in the determinations which are described in the following experimental report with reference to two figures.

Figure 2:
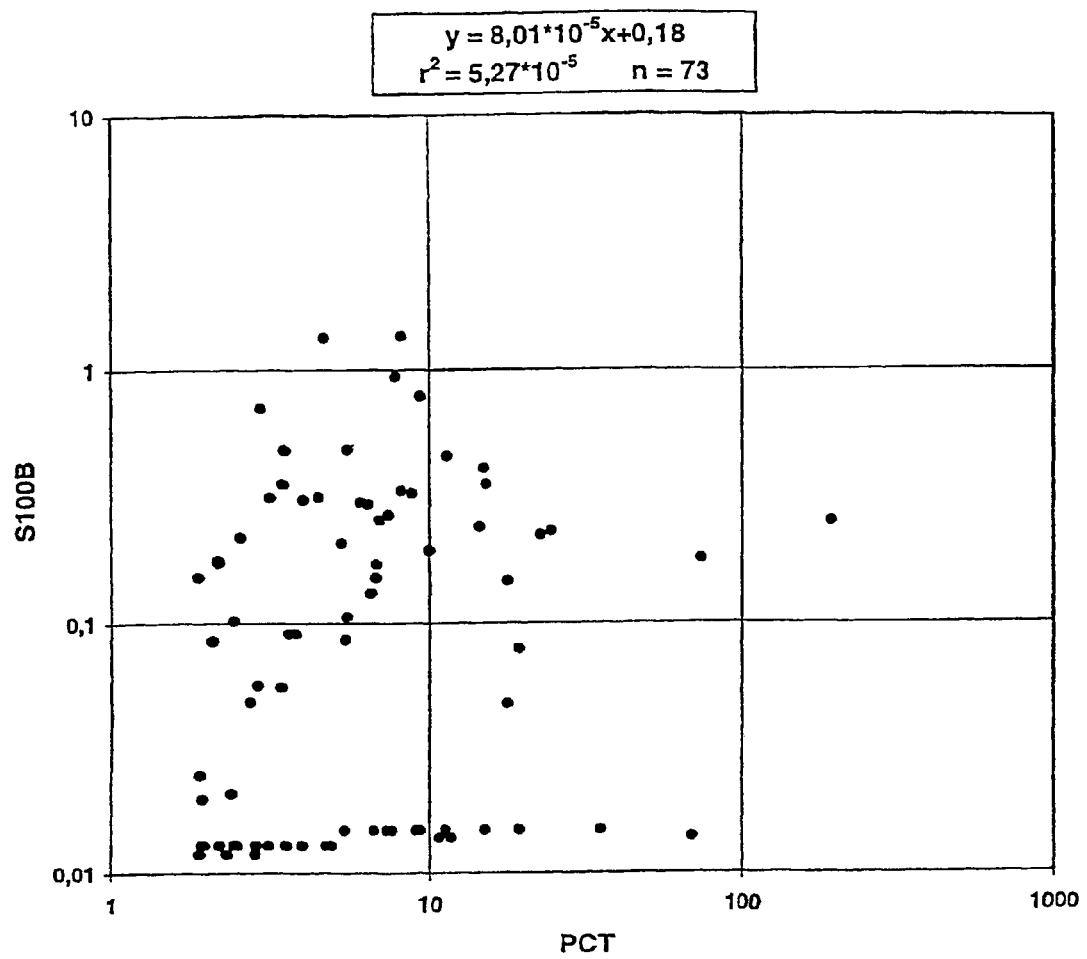

The figures show the following:

FIG. 1 shows the results of the determination of S100B in the sera of 91 sepsis patients in comparison with a group of 20 control persons (blood donors); and FIG. 2 shows the quantitative correlation of the results of the S100B determinations of the 91 sepsis patients of FIG. 1 with the results of the procalcitonin determination in the same sera.

EXPERIMENTAL REPORT

In 91 sera of sepsis patients in whom high values for the sepsis marker procalcitonin (PCT) had been found, the serum concentrations of S100B were determined using a commercial assay for the determination of S100B (Sangtec 100 IRMA, AB Sangtec Medical, Bromma, Sweden). In 64% of the sera, increased—in some cases very greatly increased—S100B concentrations (more than 0.05 µg/l) were found. On the basis of the results found, S100B may be considered as a novel acute phase protein.

A graph of the measured results is shown in FIG. 1.

If the S100B values measured for individual sera are compared with the values measured for PCT, there is no positive quantitative correlation in the sense that the highest S100B values are also found in sera in which high PCT concentrations were found. FIG. 2 shows the correlations found in the case of such a comparison. It is evident that, in the case of slightly to moderately increased PCT concentrations, it is possible to obtain S100B values which correspond to very high concentrations, whereas in a small number of cases concentrations of S100B did not reach the limit of detection of the assay used.

The substantial independence of the results of the S100B determination from those of the PCT determination shows that, in spite of the increased values for both parameters in the case of sepsis, different effects are measured, indicating that the measurement of both parameters provides more information than the measurement of only one of the parameters.

The combination of the determination of S100B with that of one or more other sepsis markers is therefore suitable for improving the fine diagnosis of sepsis and for improving the prognosis of the course of the disease and for therapy-accompanying monitoring in sepsis patients, it clearly being hoped that the interpretation of the results of such combined determinations based on the exact evaluation of individual cases documented as completely as possible (including, for example, information on the type of infection, reason for and course of the sepsis disease, characteristic data on age and sex of the patients) will steadily improve with the number of cases evaluated.

The determination of S100B can be carried out by any desired suitable detection method, but the determination in a patient's body fluid by an immunodiagnostic method using suitable selective antibodies appears to be the most advantageous from practical points of view. Commercial assays for the determination of S100B are already available and can also be used in the context of the present invention. If necessary, good accuracy of measurement in the measuring range relevant for sepsis diagnosis should be ensured.

Thus, the determination of S100B can be carried out for early differential diagnosis and for detection and for the preparation of a prognosis, for assessment of the severity and for therapy-accompanying assessment of the course of sepsis, by determining the content of S100B in such a method in a sample of a patient's biological fluid and drawing conclusions about the presence of a sepsis from the established presence and/or amount of S100B and correlating the result obtained with the severity, the progress of the sepsis and/or the tissue or organ most strongly affected by the sepsis and appropriately choosing the possible treatment and/or estimating the treatment prospects.

The invention claimed is:

1. A method for confirming a clinical diagnosis of sepsis in a patient suspected of having sepsis, comprising testing a biological fluid of said patient for the amounts of S100B and procalcitonin, and comparing said amounts to the corresponding amounts in a control sample, wherein elevated amounts of S100B and procalcitonin are indicative of sepsis.

2. The method of claim 1, wherein said biological fluid is human serum.

3. The method of claim 1, wherein said sepsis is a bacterial sepsis.

4. The method of claim 1, wherein the amounts of S100B and procalcitonin are determined by an immunodiagnostic assay method.

* * * * *